United States Patent
Kanner et al.

(10) Patent No.: US 7,070,051 B2
(45) Date of Patent: Jul. 4, 2006

(54) NEEDLE COUNTER DEVICE INCLUDING TROUGHS OF COHESIVE MATERIAL

(75) Inventors: Rowland W. Kanner, Guntersville, AL (US); Larry Lee Young, Arab, AL (US)

(73) Assignee: Atrion Medical Products, Inc., Arab, AL (US)

( * ) Notice: Subject to any disclaimer, the term of this patent is extended or adjusted under 35 U.S.C. 154(b) by 0 days.

(21) Appl. No.: 11/010,067

(22) Filed: Dec. 10, 2004

(65) Prior Publication Data

US 2005/0211588 A1  Sep. 29, 2005

Related U.S. Application Data

(60) Provisional application No. 60/556,678, filed on Mar. 26, 2004.

(51) Int. Cl.
*B65D 85/24* (2006.01)
*A61L 17/00* (2006.01)

(52) U.S. Cl. ............... 206/382; 206/63.3; 206/460
(58) Field of Classification Search .......... 206/63.3, 206/365–366, 380–383, 227, 460
See application file for complete search history.

(56) References Cited

U.S. PATENT DOCUMENTS

| | | | |
|---|---|---|---|
| 3,944,069 A | 3/1976 | Eldridge, Jr. | |
| 4,008,802 A | 2/1977 | Freitag | |
| 4,013,109 A | 3/1977 | Sandel | |
| 4,167,230 A * | 9/1979 | Barratt | 206/380 |
| 4,182,448 A * | 1/1980 | Huck et al. | 206/380 |
| 4,243,140 A * | 1/1981 | Thrun | 206/380 |
| 4,349,120 A | 9/1982 | DiNardo | |
| 4,466,541 A | 8/1984 | Tabler et al. | |
| 4,549,670 A | 10/1985 | Trendler | |
| 4,596,329 A * | 6/1986 | Eldridge, Jr. | 206/382 |
| 4,746,008 A | 5/1988 | Heverly et al. | |
| 4,967,924 A | 11/1990 | Murofushi et al. | |
| 5,869,562 A | 2/1999 | Lindquist et al. | |
| 5,938,063 A | 8/1999 | Hoftman | |

* cited by examiner

*Primary Examiner*—Bryon P. Gehman
(74) *Attorney, Agent, or Firm*—Trexler, Bushnell, Giangiorgi, Blackstone & Marr, Ltd.

(57) ABSTRACT

A needle counter device which utilizes an adhesive disposed in one or more, preferably V-shaped, troughs. The adhesive provides instant, strong grip upon contact, but also provides very low resistance to needle penetration (i.e., it is easy to stick a needle in the adhesive, but difficult to pull the needle out). The device includes a base and a lid, and opens and closes much like a book. Once the device is closed, the device tends to remain closed unless intentionally opened. A thin layer of adhesive may be provided on the inside of the lid, to retain used surgical blades, and a piece of resilient foam may also be provided for temporarily "parking" a suture needle. The sides of each trough are lined with structure which serves to prevent an accidentally laid surgical instrument from unintentionally contacting the adhesive. Numerical indices provide a quick visual, counting assist. Double sticky tape, covered with a protective peel away release sheet, can be provided on the outside surface of the lid and/or the base, for adhering the device to work surfaces.

36 Claims, 9 Drawing Sheets

NEEDLE COUNTER DEVICE INCLUDING TROUGHS OF COHESIVE MATERIAL

RELATED APPLICATION (PRIORITY CLAIM)

This application claims the benefit of U.S. Provisional Application Ser. No. 60/556,678, filed Mar. 26, 2004.

BACKGROUND

The present invention generally relates to needle counter devices used in surgery, and more specifically relates to a needle counter device which includes an adhesive disposed in one or more troughs for receiving and retaining sharps (i.e., needles, blades, etc.) during surgery.

It is important to account for and safely retain for disposal, all suture needles used in a surgical procedure. Since the quantity of needles used for any given surgical procedure can vary widely, several needles may need to be accounted for and each must be accounted for to assure none is left in the patient or in the surgical drapes, bed sheets or lost elsewhere. This protects the patient, the surgical and nursing staff as well as cleaning and laundry personnel. Scalpel blades may also be retired or changed out during procedures and thus become a hazard unless they too are accounted for. The potential for presence of blood born pathogens on these contaminated sharp objects makes their safekeeping essential so they can be disposed of at minimal risk.

Numerous needle counting device concepts already exist. Methods used to retain the sharps include use of soft penetrable foam strips, magnetic sheets, thin film adhesives, foam backed film adhesives, "piggy bank" type receiving slots and various combinations of these items. Many of these devices date back more than 30 years. Many of the devices are contained within a variation of a hinged plastic box form that opens and closes like a book. Various methods have been employed to latch or lock the box closed. Often the sharps receiving section of the needle counter is divided into numbered sections for needle placement in order to facilitate the counting process. From the user standpoint, improved means to assure and facilitate accurate counting of these needles and prevent accidental dislodgement has become more important in recent years, especially as the average age and general shortage of nursing staff means that the declining quality of the users eyesight and their need to be more efficient come into conflict.

Some examples of prior art devices can be found in U.S. Pat. No. 3,944,069 (Pressure sensitive adhesive coated foam pad); U.S. Pat No. 4,008,802 (Resilient pad with raised ridges for receiving needles); U.S. Pat No. 4,013,109 (Hinged container with magnetic surface to hold needles); U.S. Pat No. 4,243,140 (Hinged container with slotted foam ribs on one side and a thin adhesive layer on the other to hold sharps); and U.S. Pat No. 4,596,329 (Combinations of foam and magnetic media to retain sharps).

Needle counters are very much a commodity item in the health care field and as such must be made inexpensively and sold cheaply in order to compete. Recent OSHA emphasis and legislation directed toward safe handling methods and systems for contaminated sharps to prevent transfer of diseases by blood born pathogens has directed more attention upon user friendliness and ease of use of these devices. Soft foam pads require that the often curved suture needles be impaled into or through them. Some foam pads are slotted to receive the needles within their slots. Magnetic sheets are sometimes used to hold the needles. Some hybrid concepts have a thin adhesive film applied to a foam pad wherein the pad may be impaled with the needle or the needle or sharp may be retained by the adhesive on contact.

All these devices do their job with varying degrees of success: 1) The foam devices generally provide very little grip and often fail to retain needles against very low dislodging forces unless they are made of an elastomeric foam and then they require a rather high insertion force in order to deliver a high pull-out force. 2) Magnets hold the low carbon stainless needles with some degree of success but the needles typically dislodge very easily and can be pushed around and disorganized or knocked loose if even slightly disturbed. Occasionally the sharps can become magnetized from contact with the magnetic sheet whereupon they may tend to move from their assigned location and clump together which makes counting difficult, especially when very fine needles are involved. Some surgeons complain that the magnetized needles tend to attract to the needle holder forceps and become difficult to handle. Magnetic sheets are also costly and they are generally dark in color so they fail to provide good visual contrast for observing the shiny metal needles. 3) Thin film adhesive surfaces are not very compliant and therefore limited in effectiveness by the amount of surface area of the sharps they can attach to. Backing thin film adhesives with a foam pad helps assist in utilization of the adhesive but remain far from an ideal solution since the film membrane also tends to inhibit insertion of needles into the foam. Many devices have also employed an adhesive on their bottom in order to secure the device to a work surface and prevent movement during use.

OBJECTS AND SUMMARY

An object of an embodiment of the present invention is to provide a needle counter device which is configured to hold a needle fast with either minimal insertion force or simple incidental contact in order to make certain the needle remains at the location it was assigned by a healthcare worker.

Another object of an embodiment of the present invention is to provide a needle counter device which facilitates good illumination of placed needles to assure easy visibility for placement and counting at the end of the procedure.

Still another object of an embodiment of the present invention is to provide a needle counter device which is configured such that needles remain upright where they are placed and viewing them is not hampered by the background color of the retaining media.

Yet another object of an embodiment of the present invention is to provide a needle counter device which has easy to read numerical indicia.

Still yet another object of an embodiment of the present invention is to provide a needle counter device which is: very inexpensive to manufacture, constructed of very few parts, capable of being assembled in few steps, and designed such that it facilitates an automated process.

Briefly, and in accordance with at least one of the foregoing objects, an embodiment of the present invention provides a needle counter device which utilizes an adhesive disposed in one or more troughs. Although the troughs may be provided in many different cross-sectional shapes, preferably the troughs are V-shaped to conserve the amount of adhesive which must be provided to fill the troughs. The adhesive provides instant, strong grip upon contact, but also provides very low resistance to needle penetration. In other words, it is easy to sink a needle in the adhesive, but difficult to pull the needle out of the adhesive. The adhesive may be a synthetic polymer "hot melt" adhesive which quickly conforms to the needle surface and, due to its low durometer, displays remarkable adhesion to even very fine needles delivered with a force equal to no more than the needle's own weight. Preferably, properties of the adhesive are such that tugging upon an applied needle tends to cause the adhesive to elongate at the attachment or "pull legs" in such a manner that the needle, when released, is elastically withdrawn back to the adhesive surface. Preferably, the adhesive is thicker than that of the common film type, and is injected into the trough(s), such that the aspect ratio of the applied adhesive is more like that of a bead than that of a film. The adhesive material may be applied in a manner such that it visibly rises above the housing surface to present a good thick target for either inserting the needle or simply laying it against the tacky surface. Out of economic necessity, preferably the device is designed for ease of manufacture and assembly in order to facilitate automated construction.

BRIEF DESCRIPTION OF THE DRAWINGS

The organization and manner of the structure and operation of the invention, together with further objects and advantages thereof, may best be understood by reference to the following description, taken in connection with the accompanying drawings, wherein.

DESCRIPTION OF ILLUSTRATED EMBODIMENTS

Figure 1:
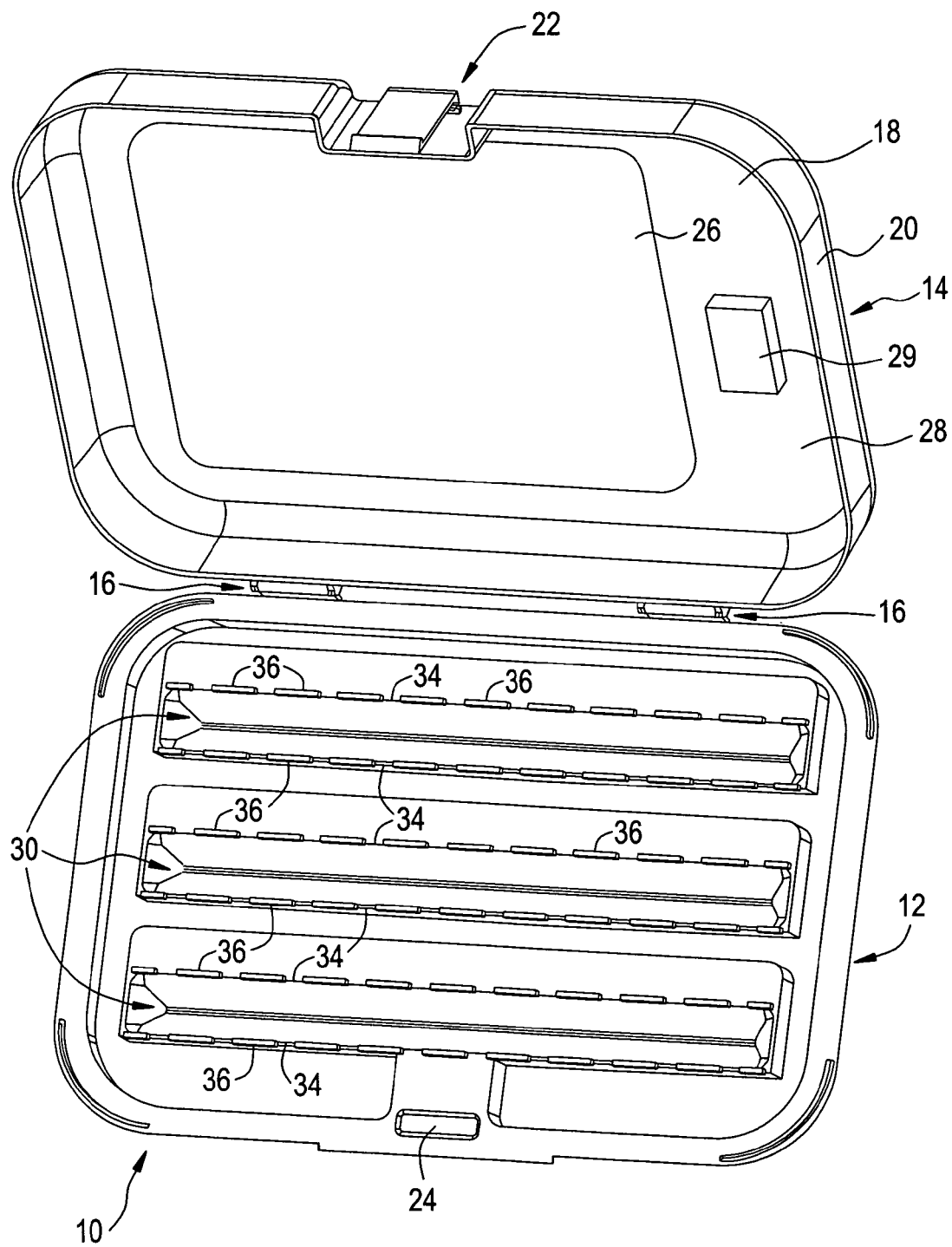
FIG. 1 is a top perspective view of a needle counter device which is in accordance with a preferred embodiment of the present invention, showing the device partially open.

While the invention may be susceptible to embodiment in different forms, there are shown in the drawings, and herein will be described in detail, specific embodiments of the invention. The present disclosure is to be considered an example of the principles of the invention, and is not intended to limit the invention to that which is illustrated and described herein.

FIGS. 1–6 illustrate a needle counter device 10 which is in accordance with a preferred embodiment of the present invention. The needle counter device provides a mechanism that holds a needle fast with either minimal insertion force or simple incidental contact in order to make certain the needle remains at the location it was assigned by a healthcare worker. The needle counter device also facilitates good illumination of placed needles to assure easy visibility for placement and counting at the end of the procedure. Further, the needle counter device provides that needles remain upright where they are placed and that viewing them is not hampered by the background color of the retaining media. The device is very inexpensive to manufacture, is constructed of very few parts, is capable of being assembled in few steps, and is designed such that it facilitates an automated process.

In connection with describing the needle counter devices, terms such as needles, blades, sharps, etc. are used with the understanding that the needle counter device is meant to be used in association with any surgical device, such as one having a sharp edge or point, which a healthcare provider may want to keep track of during surgery.

As shown in FIGS. 1–5, the needle counter device 10 includes a base 12 and a lid 14 which is pivotably connected to the base 12, such that the device 10 can be opened and closed much like a book. The base 12 and lid 14 may be of a two piece construction having a snap together assembly, thereby forming one or more hinges 16. Alternatively, the device could be constructed of a one piece molded form, connected by means of an integrally molded living hinge. Regardless, preferably the device 10 is very inexpensive to manufacture, constructed of very few parts, capable of being assembled in few steps, and designed such that it facilitates an automated process.

Preferably, the lid 14 provides a generally planar main body portion 18, and an upstanding side wall 20 which is disposed about the periphery of the main body portion 18. Latch structure 22 is preferably provided on the lid 14 and a corresponding hole 24 or other corresponding structure is provided on the base 12, such that the device 10 can be closed, and tends to remain closed unless intentionally opened. The lid 14 is preferably approximately two thirds of the overall height of the device 10 when the device 10 is closed. This provides head space clearance under the lid 14 to close upon and contain captured suture needles retained by the base 12.

Figure 2:
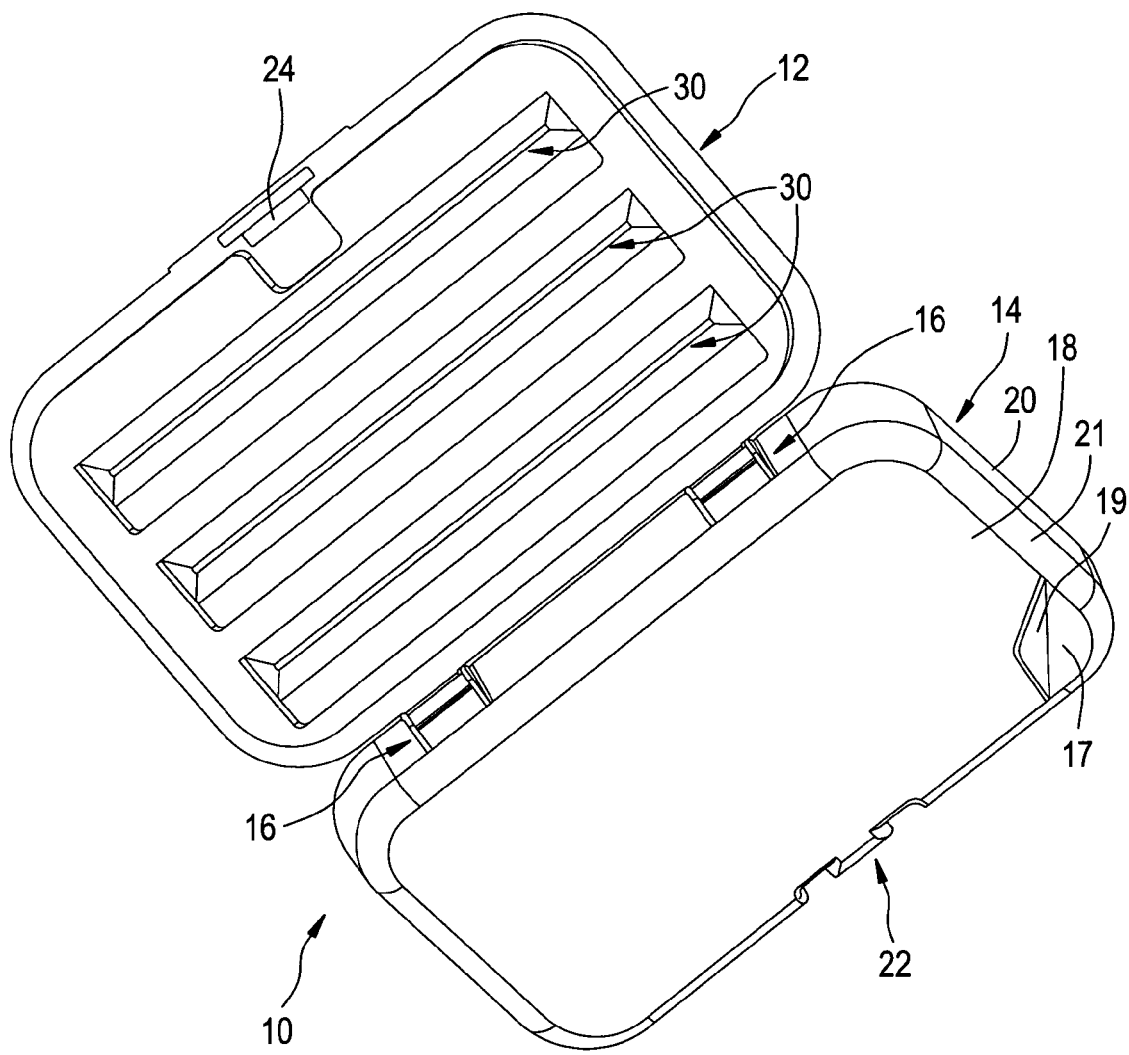
FIG. 2 is bottom perspective view of the needle counter device shown in FIG. 1, showing the device partially open.

As shown in FIG. 2, an adhesive layer 17 with a peel away covering 19 may be provided on the outside surface 21 of the lid 14, wherein in use, a user can peel away the covering 19, thereby exposing the adhesive layer 17, and the adhesive layer 17 can be pressed to a surface, thereby securably, but removably, mounting the needle counter device 10 to the surface.

As shown in FIG. 1, a thin layer of adhesive 26 may be provided on the inside 28 of the lid 14, to retain used surgical blades. Alternatively, layer 26 can be a magnetic surface. Additionally, a piece of resilient foam 29 may be provided on the inside 28 of the lid 14, wherein the foam may be used for temporarily "parking" a suture needle, if desired. Needles having suture attached and still in use may be "parked" into the foam until time to finish using the suture. As will be described more fully below in connection with FIG. 9, the foam 29 may be provided as having an array of holes to facilitate removal of parked needles and scalpel blades.

Figure 3:
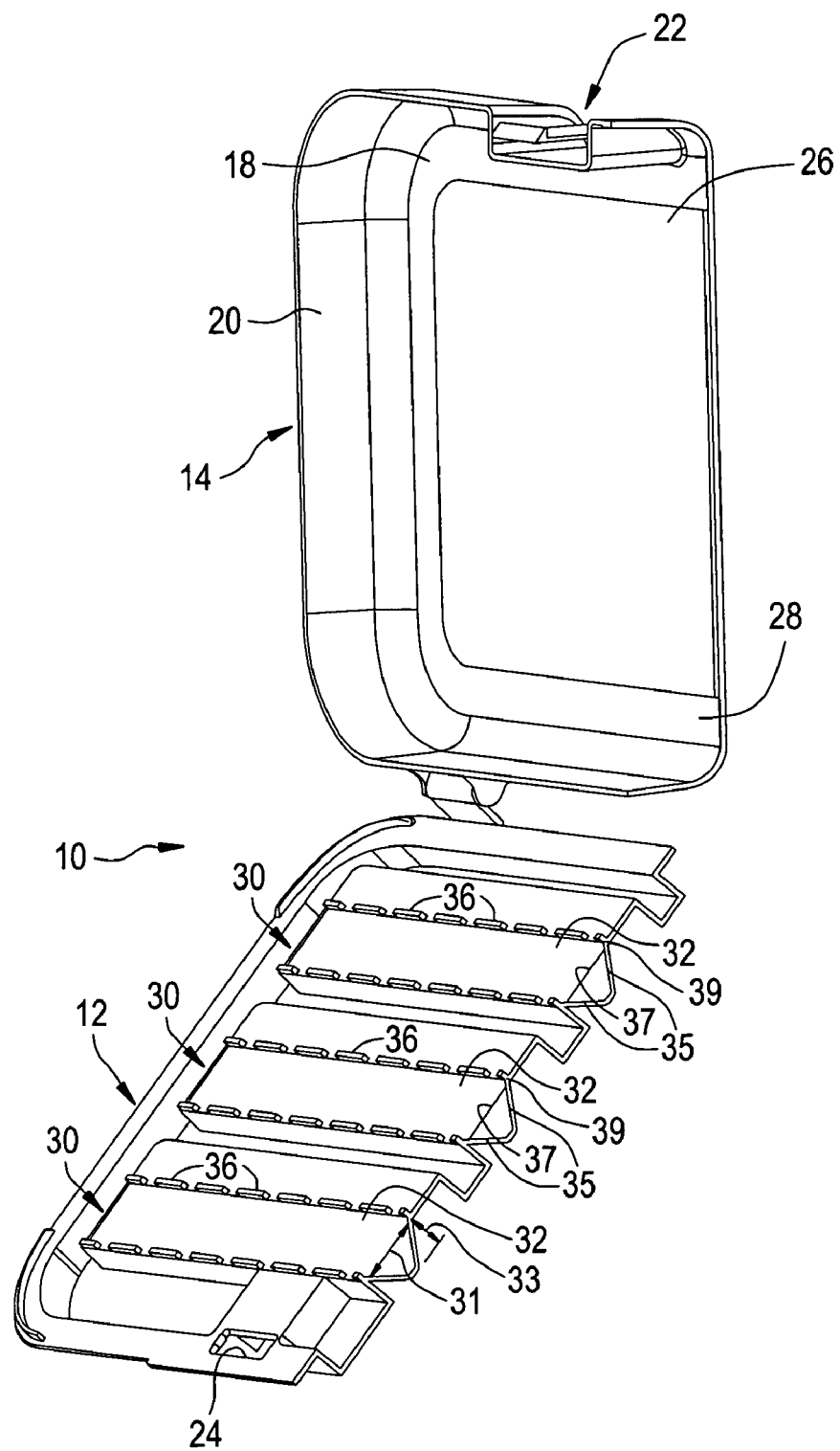
FIG. 3 is a view similar to FIG. 1, but showing the device in transverse section.
Figure 4:
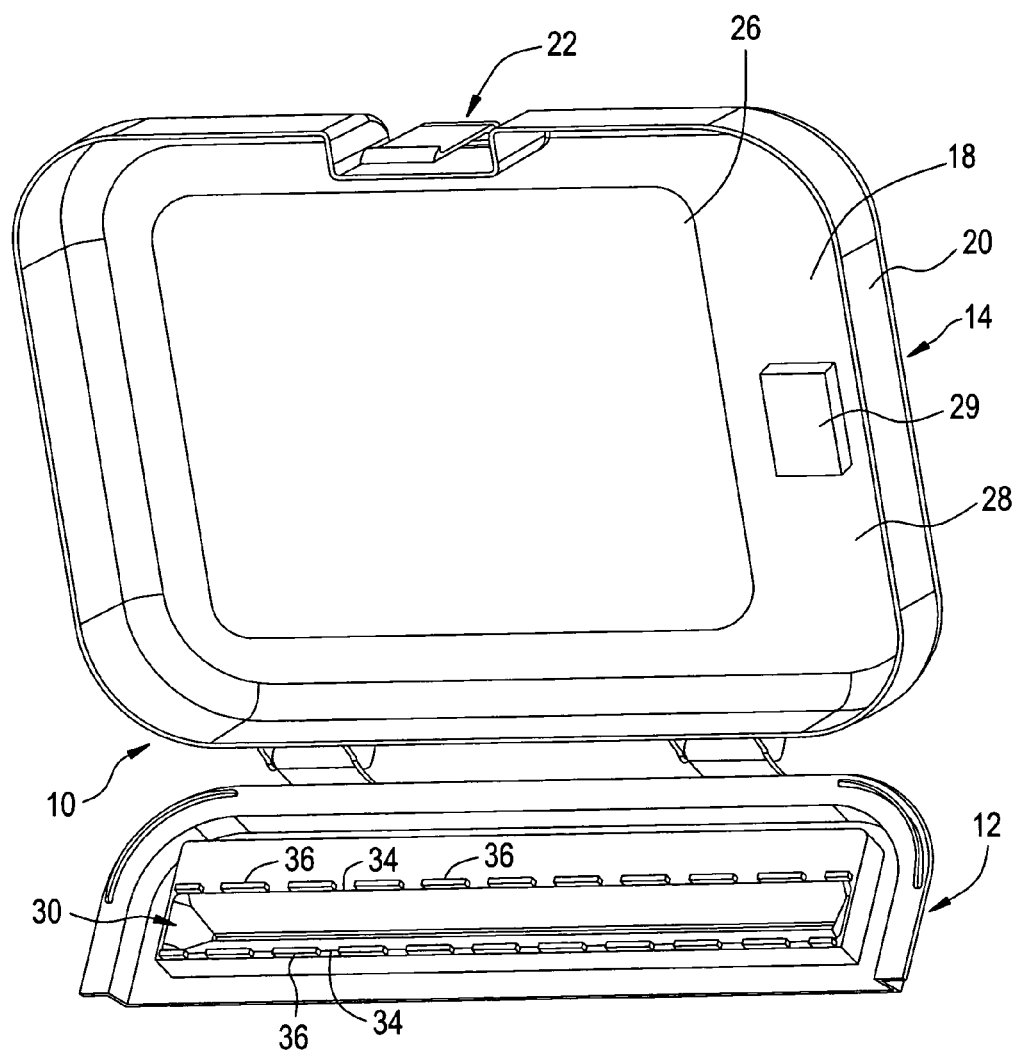
FIG. 4 is a view similar to FIG. 1, but showing a base of the device in longitudinal section.
Figure 5:
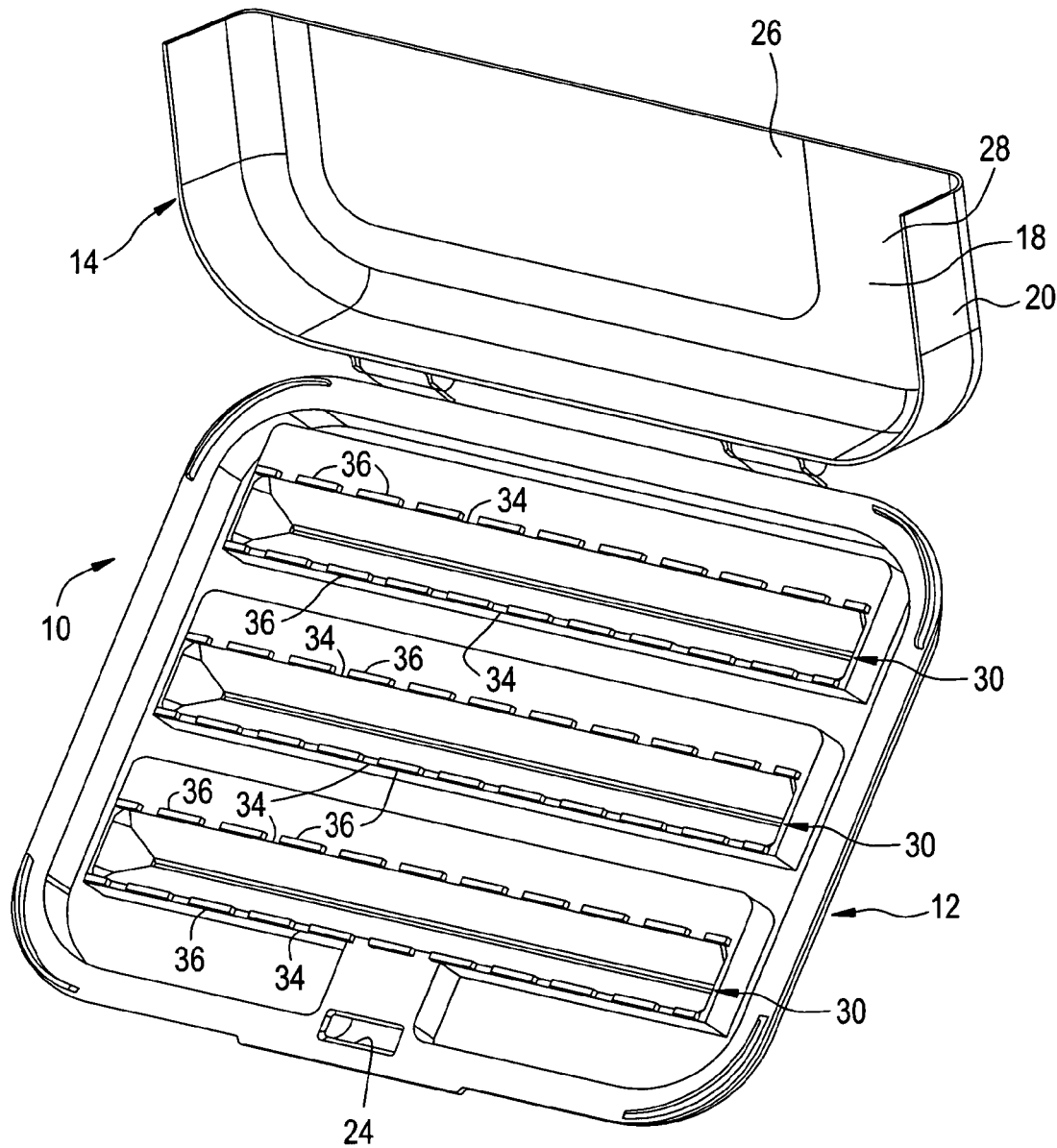
FIG. 5 is a view similar to FIG. 1, but showing a lid of the device in longitudinal section.
Figure 6:
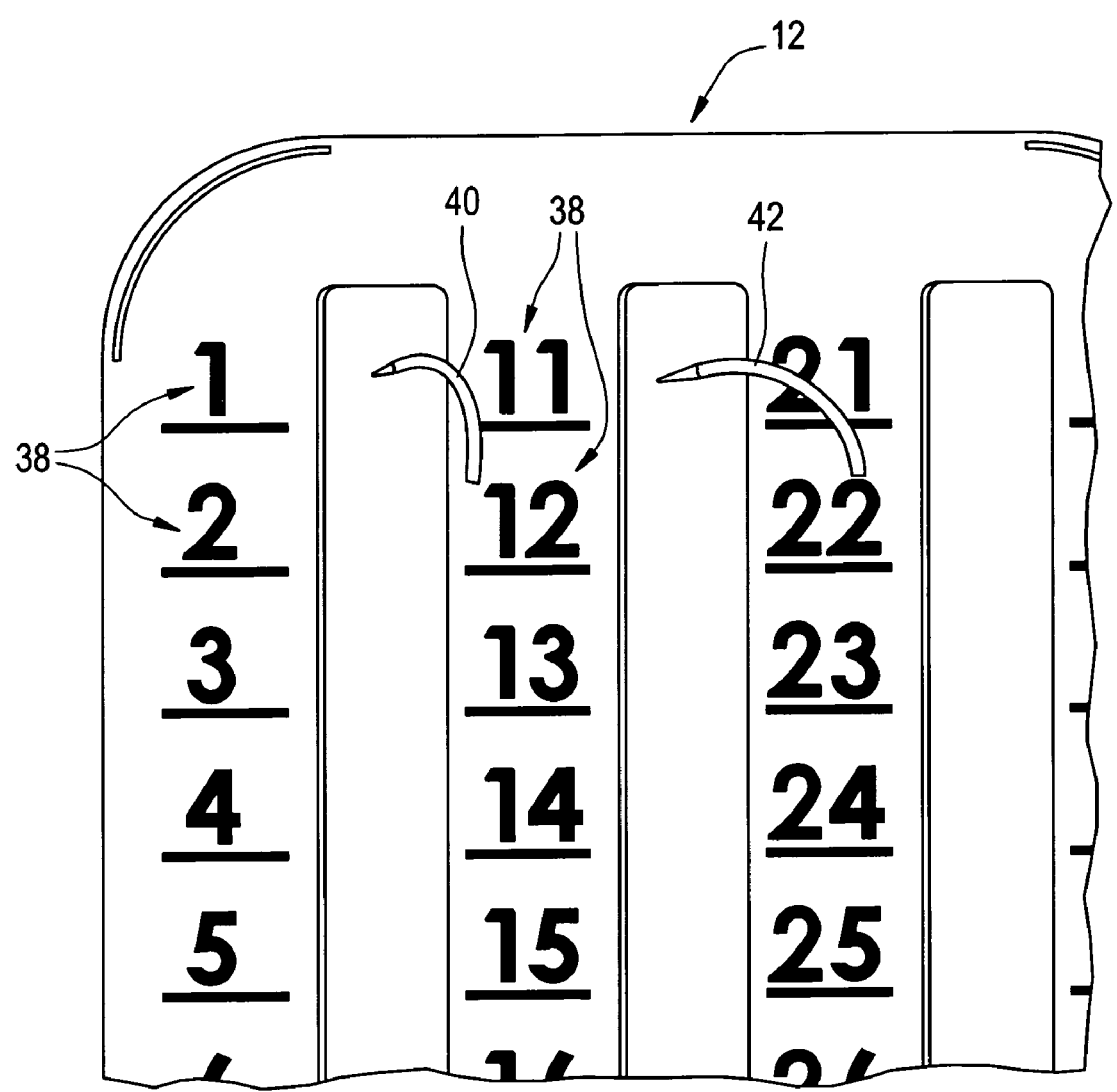
FIG. 6 is a close up view of the needle counter device, showing an inserted needle at location 1 and a laid down needle at location 11.

The base 12 is preferably generally flat, but includes one or a plurality of troughs 30 which are filled with a sticky elastomeric, sharps retaining media or adhesive 32 (due to the need to illustrate detail of the troughs themselves in FIGS. 1, 4 and 5, the adhesive is only shown in FIGS. 3 and 6). Preferably, the top surface 37 of the adhesive 32 is below the top 39 of each trough 30, as this takes less material, as well as prevents needle holders and other instruments, sutures, surgical garments and the like from inadvertently coming into contact with the sticky adhesive.

The troughs 30 may be formed in a variety of cross-sectional shapes. FIGS. 1, 3, 4 and 5 illustrate the troughs 30 as having a V-shaped cross-section, and such shape is preferred. The V-shape trough is configured to provide the necessary depth for burying needle tips and sufficient width to provide a reasonable target for users to hit. Nevertheless, other shapes, such as rectangular-shaped cross-section troughs, are entirely possible. While it is possible to provide troughs having a rectangular-shaped cross-section, that troughs formed in the V-shaped configuration will save considerably in adhesive usage compared to a same-width rectangular trough design.

Not only are the troughs preferably V-shaped, but preferably each trough 30 is relatively narrow having a width (dimension 31 in FIG. 3) of, for example, 0.150 inches. The depth (dimension 33 in FIG. 3) of each trough 30 may be 0.190 inches, while the depth of the adhesive may be, for example, 0.120 inches. The adhesive may be provided as being even more shallow, such as shallow as 0.060 inches in height. Not only do narrow troughs 30 filled to a low level with adhesive 32 cost less to manufacture, but narrow trough 30 tend to provide that needles inserted into the adhesive 32 are retained in an upright position by the sidewalls 35 (see FIG. 3) which define each trough 30. If the troughs are provided as being too wide, needles which are inserted into the troughs may lay over, leaving them harder to count. As a result of providing that the troughs are narrow, and the sidewalls 35 closer together, inserted needles array in a much more vertical and orderly fashion for quicker recognition and counting. This greatly benefits the user.

Additionally, due to the troughs 30 being narrow, needles will tend to be inserted longitudinally instead of transversely into the troughs 30. Hence, guidance of the needles is assisted by the sidewalls 35. Furthermore, the needles can if desired, be pressed downward deeply into the adhesive 32 instead of being speared into it. This makes the needle-delivery process very easy.

Regardless of the shape of the troughs 30, preferably the sides 34 of each trough 30 are lined with a low interrupted rib or series of spaced apart pickets 36 which serve to prevent an accidentally laid surgical instrument from unintentionally contacting the adhesive 32. Preferably, numerical indices 38 are provided alongside each trough 30 to provide a quick visual assist to the counting process at the conclusion of the procedure. For simplicity, the indices 38 are shown only in FIG. 6. Although the troughs 30 are shown as being vertical relative to the indices 38, they may be provided as being horizontal instead. An example of the function of the ribs 36 and numerical indices 38 is illustrated in FIG. 6, wherein a needle 40 has been inserted in the adhesive 32 at location 1, and another needle 42 has been laid down upon the adhesive at location 11. Ideally, the base 12 is of a color, such as red, which facilitates good illumination of placed needles to assure easy visibility for placement and counting at the end of the procedure. Additionally, preferably the adhesive 32 is translucent and provided in a color, such as a honey color, which does not hamper plain viewing of the needles.

Preferably, the adhesive 32 which is retained in the troughs 30 is a very high tack, one part, pressure sensitive elastomeric adhesive, and is such that it can be easily delivered to the trough(s) hot, whereupon it quickly sets as it cools. Preferably, the adhesive 32 is clean and does not require curing, solvents or fume handling, and is therefore stable and ideal for use in a simple automated in line assembly system. This type of adhesive is well suited to the thick application required by the trough design. Preferably, the adhesive is homogeneous. Many different adhesives may be used in association with the present invention. The adhesive may be as described in U.S. Pat. No. 5,869,562 (see specifically Example 2). U.S. Pat. No. 5,869,562 is hereby incorporated herein by reference in its entirety.

Major benefits of the adhesive-filled trough approach include: 1) Provision of a deep adhesive pool into which a point of a needle can be inserted for capture by means of bonding; 2) Provision of a sufficient adhesive volume to allow large elastic excursions in order to hold onto and resist removal of any needle the adhesive has become attached to; and 3) Very high initial tack under conditions of minimal needle contact pressure.

The adhesive-filled trough approach is designed to exploit both manufacturing and performance benefits of 100% solids content, fume and solvent free, rapid setting, elastomeric, pressure sensitive adhesive (PSA) materials that can be rapidly applied into deep troughs within the needle counter. The strength of an adhesive bond is generally understood to be proportional to the area in contact, thus more area translates directly into a stronger connection. Adhesive thickness has a significant effect on peel strength of a bond as well. This is due to the viscoelastic nature of the adhesive. With elastomeric adhesives, thicker bondlines will generally result in higher peel strength. Viscoelastic adhesives also perform better when loaded in a shear condition than in a peel condition.

The nature of the needle counter design provides for a much larger needle surface area to be contacted, wetted and gripped by the adhesive. That is because the needle's tip can be immersed deeply into an adhesive filled trough, wherein adhesive is not only tacky upon its surface, but internally as well. The entire buried surface of the needle tip is therefore in full contact with tacky adhesive. By comparison, thin film adhesives applied to foam, membrane or paper substrates of prior art needle counters provide minimal bondline thickness. In some prior art needle counter configurations, the adhesive contact area against the piercing needle is little more than the circumference of the needle multiplied by the thickness of the adhesive film.

The design also allows the adhesive's viscoelastic properties to be fully exploited as part of the retention mechanism by minimizing restrictions against the adhesive's elongation, should a needle be pulled upon. Elongation for these adhesives can run from 500% to 5000%. This freedom to elongate or stretch in response to loading, resists needle pull-out by keeping the adhesive in shear longer, extending the nucleation phase and delaying the onset of bond failure due to peeling. Conversely, the paper or foam substrates of prior art examples, serve to rigidize the adhesive film layer. Therefore, the amount of adhesive available to elastically feed or extend itself under load is less since this property depends upon adhesive thickness. As a consequence, nucleation peaks early, hastening the onset of bond failure. Under use conditions, with thin rigidized adhesive films, very little travel distance is permitted by the substrate before elongation and peel limits are reached. The rigidized adhesive films let go much sooner due to their inability to delay peel by extending themselves elastically. The negative consequence of resistance provided by the rigidizing substrate is that the adhesive is thrown out of shear and into a peel condition sooner. An additional advantage of the above-described design, using a deep trough of adhesive instead of the conventional thin film adhesive, is the minimization of adverse performance resulting from any degradation of surface tack due to storage or environmental conditions.

Figure 7:
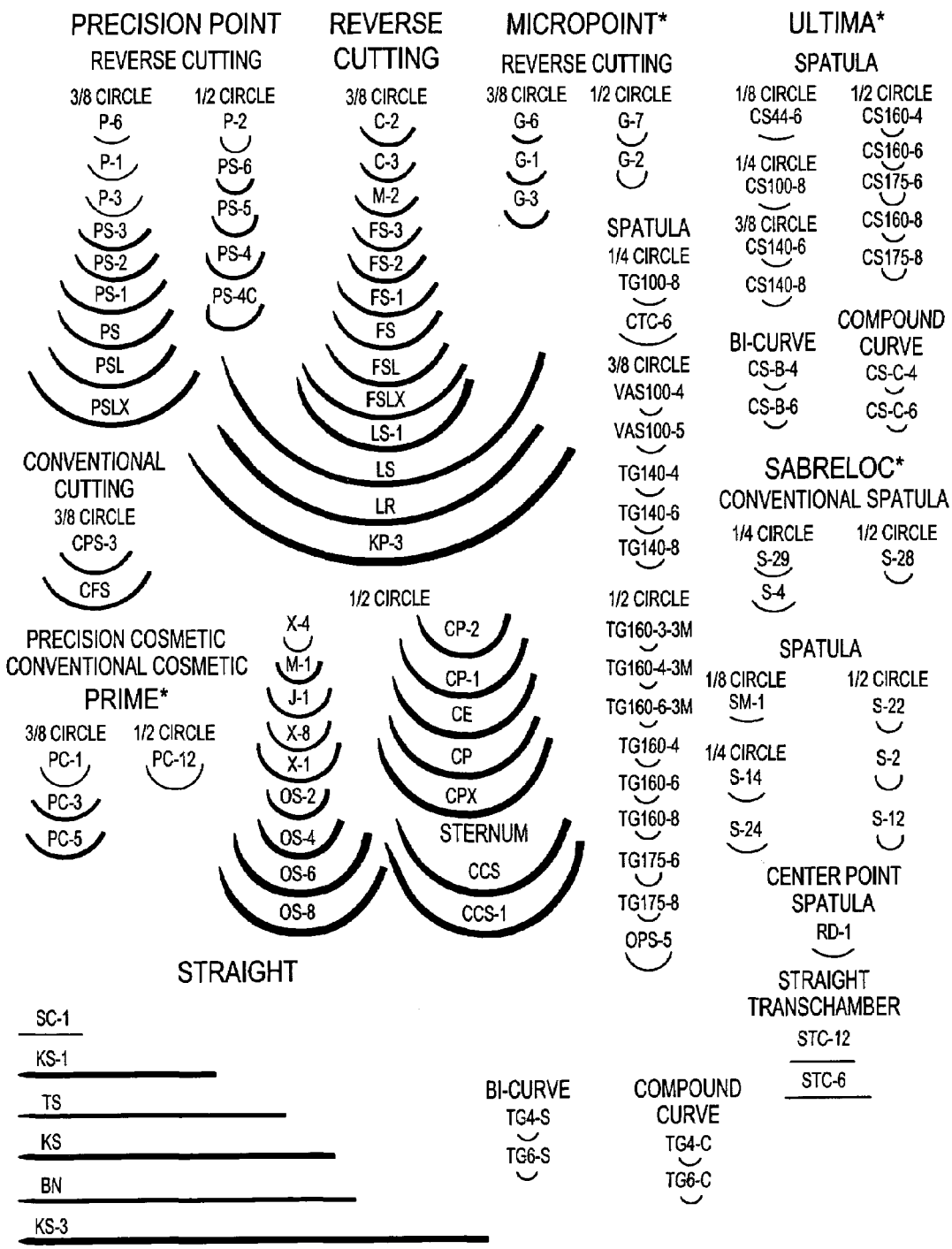
FIGS. 7 and 8 illustrate a range of needle types offered by a vendor in the marketplace.
Figure 8:
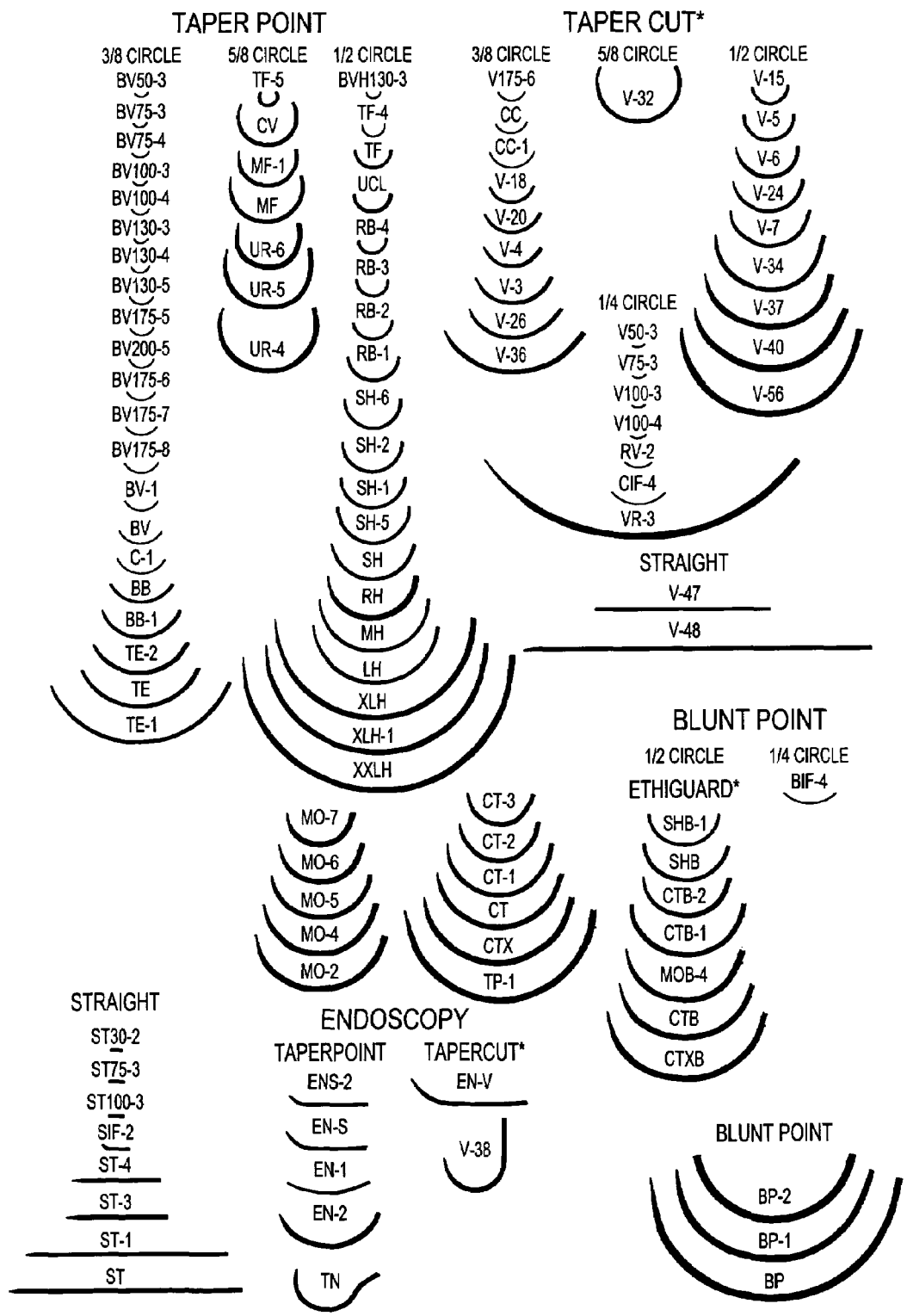

The preferred adhesives for the needle counter device also must be suitable for penetration by any needle type used during a medical procedure. Since the variety of needles available is virtually limitless, adhesive used in this application must be receptive to very sharp needles ranging from 0.009" diameter needles half the size of an eyelash, to blunt tipped safety needles 0.062" in diameter (see, for example, FIG. 7 and 8 which illustrate one vendor's needle types). All needle types must be accommodated and the insertion force to penetrate into the adhesive must not be excessive. The penetration requirements for these needles mean that the adhesive used in a needle counter device should be soft and stable and not be so tough so as to make needle insertion difficult. Substrate backing materials of some prior art devices also tend to reinforce and toughen the immediate underlying surface against needle penetration. Very small and blunt safety type needles are particularly difficult to insert through this reinforced underlayment. The needle counter device design described herein provides a deep homogeneous body of adhesive to receive the needle that is free of any tough reinforcing surface underlayment and therefore highly receptive to all needle types. The ideal adhesive for this application possesses sufficiently low durometer and puncture resistance at its surface under use conditions, to facilitate easy needle insertion. Experience has shown that adhesives having a durometer ranging from 10 to 24 Shore "A", and preferably in the range of 12 to 20 Shore "A", work well in this application.

PRESSURE SENSITIVE ADHESIVES (PSAs). PSAs are generally defined as being permanently tacky, requiring no activation by water, solvent or heat. They are inherently soft materials formulated to provide a balance of adhesive properties and cohesive strength. This balance depends upon the viscoelastic nature of the adhesive as well as the additives used in its formulation. The primary mode of bonding for a pressure sensitive adhesive is not chemical or mechanical but rather a polar attraction of the adhesive to the substrate. Pressure is required to provide sufficient wet-out onto the substrate surface to provide adequate adhesion. Cohesion or internal strength of the adhesive must be high enough to resist creep and shear stresses in the end use application.

With PSAs, surface energy of the intended substrate may dictate the type of base polymer to be used. Polar polymers such as acrylics adhesives have a tendency to adhere best to high surface energy substrates (e.g., metals, glass, etc.) by virtue of their dipole-dipole interaction and/or hydrogen bonding. Non-polar adhesives tend to adhere to both low (e.g., plastics and EPDM rubber) and high surface energy substrates.

Hot melt adhesives are composed primarily of thermoplastics or materials which appear to be thermoplastic. Elastomer based PSAs typically have a synthetic rubber as the base polymer. Styrene block copolymers or styrene butadiene rubbers are commonly used as the synthetic base resin in these formulations. Styrenic block copolymer (SBC) is synthesized via anionic polymerization such as styrene-isoprene (SIS) or strenebutadiene-styrene (SBS). SBCs offer high cohesive strength similar to that of chemically vulcanized rubbers, yet because the crosslinks in these polymers are physical rather than chemical, they are reversible allowing liquid like flow when heated above the glass transition temperature (Tg) of the polystyrene molecular endblocks. Some polyamide polymers are also formulated for high performance hot melt PSAs. Ethylene vinyl acetate (EVA) based adhesives are the most common general purpose type of hot melt, but suffer from poor adhesion to low energy substrates. Other hot melt resin bases are used but are probably not as well suited to the needs of the needle counter device described herein as SBC and polyamides. Since a low melt viscosity is required, most polymers used as bases for hot melt adhesives are semi-crystalline in character.

SBCs are best known for their low temperature flexibility combined with heat resistance and most types are used for pressure sensitive applications. Most block copolymers can be mated after the adhesive has cooled. Polyamides are high performance hot melts that are used when bonds need to resist high temperatures (up to 350 F.) as well as fuels or solvents. They are among the strongest hot melt adhesives and can be formulated to be soft and tacky or hard and rigid depending on the polymer and the resin used.

Typical performance characteristics for SBCs and polyamides are:
1. High heat resistance.
2. Excellent cohesion strength.
3. Excellent peel strength.
4. High tack—Excellent quick adhesion.
5. Low volatile emissions.
6. Low post application shrinkage vs. solvent based adhesives.
7. Achieve high viscosity very quickly after application.
8. High solids content facilitates extremely thick applications.
9. Non-polar in nature provides adhesion to both low-surface energy non-polar substrates and high surface energy polar substrates.

Tg. Hot melts are characterized by their glass transition temperature (Tg) which is actually a composite of several physical attributes. It reflects behavior of the adhesive and is a way of understanding the molecular motion that occurs in a polymeric system which is a fundamental concern when considering adhesion, cohesion and other properties of polymers. At low temperatures, a polymer exists as a solid in which the molecular segments vibrate gently and independently. As the temperature is increased, a point is reached at which the molecule suddenly becomes more flexible and mobile. This increased flexibility occurs when the molecular vibrations become strong enough to shake the adjacent chain segments apart and allow molecules the freedom to slip by one another. The temperature required for this to occur is known as the glass transition temperature, Tg. It is a transition of the polymer from a glassy to a rubbery state where, as the temperature is raised further, the distance between the molecular segments is increased. This can be observed as a distinct increase in the slope of the polymer's volume as a function of temperature. The transition reverses upon cooling.

Tg and COHESIVE PROPERTIES. The strength of a crosslinked adhesive at elevated temperatures is very much indicated by its Tg. The Tg should be above the upper use temperature of the adhesive for good bond strength and creep resistance. Peel strength however, will be low when Tg is appreciably above the upper use temperature and low temperature performance of a relatively high Tg adhesive is limited due to brittleness. In general, an adhesive's joint strength increases and is maximized near the Tg.

Tg and PRESSURE SENSITIVE PROPERTIES. Two requirements for PSA is that it must undergo plastic flow on contact and that it must wet the substrate surface. Polymeric materials can only be pressure sensitive (flowable under slight pressure) above its Tg. Thus, most PSA materials have a Tg near or below room temperature. Having a Tg below room temperature does mean that these adhesives will not achieve high cohesive strength since in this rubbery state the molecules are also mobile enough to flow under load until the bond fails. The ideal Tg is therefore a compromise based on performance needs and is therefore preferred to be around −29 to −5 degrees C. It can be adjusted through formulation, but generally, low Tg values ensure very high tack, and medium Tg gives optimum peel and acceptable cohesive strength. Plasticizers and flexibilizers can be added to lower the Tg of the adhesive polymer by inserting a cohesively weak region of material between the base polymer molecules.

TACKIFYING RESINS. Tackifying resins can also be added to improve the "quick grab" of the adhesive by reducing the viscosity of the polymer to give faster, more complete wetting of the substrate and to raise the Tg of the adhesive (plasticizers accomplish the first objective but not the second). Reducing the viscosity makes bond formation easier and raising the Tg makes the bond failure more difficult. Wetting is improved when the adhesive polymer is fluid and in a molecularly mobile state in which the molecular motion allows the adhesive to compete with contaminants for attachment to surface sites.

MECHANISMS of TACK. Tack is defined as the property than enables an adhesive to form a bond of measurable strength with the surface of another material upon brief contact and under high pressure. Implicit is that the adhesive separates cleanly from the surface, without any macroscopic residue. Tack consists of two processes. The first is a bonding process resulting from adhesive deformation and flow into contact with the substrate to allow attachment through polar attraction, after which the second phase, a deformation or debonding process can occur in which the adhesive separates by peeling from the surface. Tack or resistance to separation of the substrate depends upon:

1. Ease of deformation, or in our application, penetration of the adhesive during the bonding stage (this determines the amount of area of interfacial contact over which the forces of polar attraction can develop).

2. The resistance to separation of contact areas.

3. The degree of deformation of the adhesive and, hence, the amount of energy dissipated as frictional heating during the debonding process.

Obviously, quantifying the tack property is greatly influenced by the experimental method and parameters. It depends not only on the nature of the PSA and the adherend, but also on pressure and time of contact. Moreover, because the response is a viscoelatic response, the temperature and the rate of debonding play a key role in the strength measured. In other words, tack is defined by the test used to measure it. So, it is important to know what kind of tests are used, what kind of information is given, and their limits.

Related standards are published by national groups, such as ASTM, and by professional associations. Normalized tests are well defined and require equipment that is easily available. They are a bridge between laboratories, users, distributors, etc. in the industry. Examples of standard tack tests include the rolling ball tack test, loop tack test, peel tack test, and probe tack test. Descriptions of such standard tests can be readily found in the industry, and specifically on the Internet. Specifically, descriptions can presently be found, for example, at www.specialchem4adhesives.com. Equipment for performing these standard tack tests can also easily be found in the industry (i.e., rolling ball tack testers, loop tack testers, probe tack testers, etc. are readily available in the marketplace).

BOND FAILURE UNDER LOAD. The phenomena observed during the separation of an adhered body and a tacky adhesive follows a pattern in which:

a) Initially, as the adhered body is withdrawn, stress increases linearly with displacement of the body.

b) Then, stress begins to increase at a non-linear rate due to nucleation (the appearance of voids at the interface).

c) The force reaches a maximum when nucleation stops.

d) Then a decrease in stress occurs as cavities, perpendicular to the interface start to grow.

e) Debonding then begins to occur as either, 1) the voids grow until coalescence occurs and stress decreases to zero (adhesion failure), or 2) cavities grow to a critical size, fibrillation appears and the fibrils lead to either adhesion failure or a cohesive failure within the adhesive.

MEASUREMENT of TACK. Tack is defined by the test used to measure it. A brief explanation of common measuring methods relevant to the present application are discussed below:

1. ROLLING BALL TACK TEST (RBT). This simple, frequently used test is one of the oldest. It gives a good idea of the adhesive behavior and is readily understood. It provides a quick comparison of high-tack adhesives. The distance a ball rolls down a ramp is inversely proportional to tackyness; the greater the distance, the less tacky the adhesive.

In the procedure, a rolling object (typically a steel ball) is placed at the top of an inclined track pursued by a horizontal, upward-facing adhesive. The ball is allowed to roll down the track and the relevant measurement is the distance,the ball travels along the adhesive surface. The test method is outlined in ASTM-D 3121.

2. PROBE TACK TEST. Analogous to pressing a thumb into the adhesive and withdrawing it, this test allows more precise and reproducible results. Mechanical probe tack testers bring a probe (ball or cylinder of various materials) into contact at a controlled rate and pressure, wait a given delay, and measure the force needed to pull away at a specified rate. The test method is based upon ASTM-D 2979-00, based on the Polyken Probe Tack test.

Other tests commonly associated with hot melt PSAs include:

VISCOSITY, to determine the molten viscosity of the hot melt adhesive at a specified temperature. ASTM-D 3236-88

RING and BALL SOFTENING POINT (RBSP), to determine the softening point of a hot melt adhesive. ASTM-E 28-67

SHEAR ADHESION FAILURE TEMPERATURE (SAFT), to test heat resistance of hot melt adhesives in the shear mode under a predetermined load and constantly rising temperature. ASTM-D 4498-85.

180 DEGREE PEEL, to test adhesion of pressure sensitive adhesives to stainless steel panels or high density polyethylene (HDPE) panels. ASTM-D 3330.

STATIC SHEAR TIME TO FAILURE, to test creep resistance of hot melt adhesives in the shear mode. ASTM-D 2294 and PSTC-7.

MELT FLOW INDEX (MFI), to determine the relative viscosity of thermoplastic polymers (related to molecular weight and structure of a polymer). ASTM-D 1238-9

Desirable physical properties for the adhesive used in connection with the needle counter device shown in FIGS. 1–6 and described hereinabove are:

| | | |
|---|---|---|
| 1. | Type: | Hot Melt PSA, high tack |
| 2. | Ingredients: | Approved under Fed. Reg. 21 CFR 175.105 |
| 3. | Ring & Ball SP: | 180° F. (82° C.) to 212° F. (100° C.) |
| 4. | Withstand Sterilization: | ETO, Gamma, E-Beam |

-continued

| 5. Color: | Light for visualization of needle |
|---|---|
| 6. SAFT degrees F: | 151F +/− 2F (Static Adhesion Failure Test) |
| 7. 180 degree peel lbs./inch | =/>3.2 |
| 8. Looptack oz./inch | =/>86 |
| 7. Polar Nature of Polymer: | Non-Polar preferred, polar possible |
| 8. Viscosity: | (Brookfield RVT) |
| 300° F. (149° C.) | 10,000 (cP)–16,000 (cP) |
| 350° F. (177° C.) | 3,600 (cP)–6,600 (cP) |
| 9. Tg: | −20° F. (−29° C.) to 23° F. (−5° C.) |
| 10. Durometer Range: | 12 to 20 Shore "A" |
| 11. Rolling Ball Tack: | N.A. |
| 12. Probe Tack: | N.A. |
| 13. Application Temp.: | <375° F. (177° C.) |

Various surgical blade types are often used during a surgical procedure. Blades of differing styles may be periodically exchanged on the scalpel handle, the removed blade being set aside for reuse later. In these instances, the thin adhesive layer 26 within the needle counter lid 14 would not be suitable for temporary parking. Layer 26 can be provided as being a magnetic sheet. However, while magnetic force tends to retain the blades well enough, the thin blades prove hard to pick up off such a magnetic surface.

Figure 9:
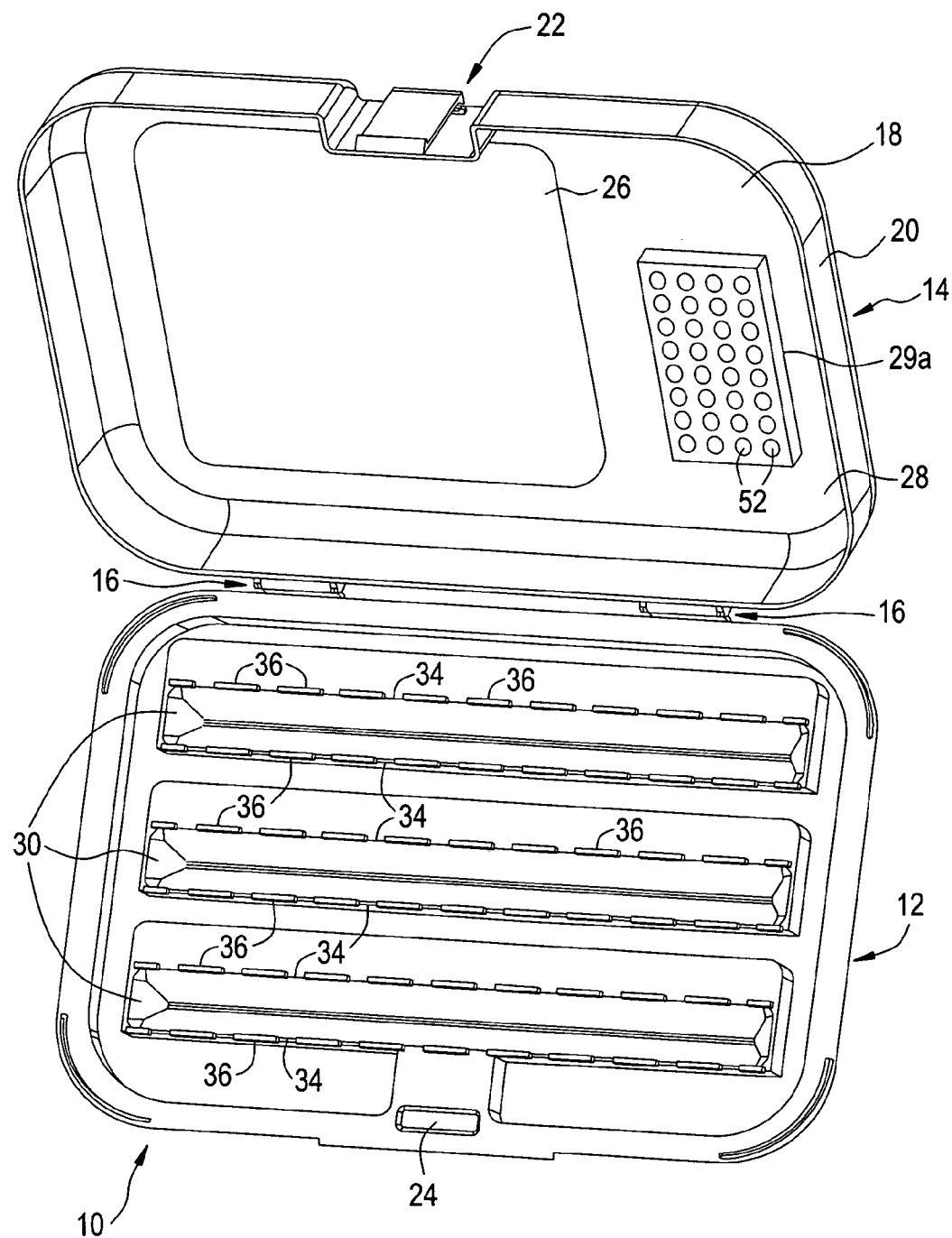
FIG. 9 illustrates a needle counter device which is in accordance with an alternative embodiment of the present invention, wherein a large foam pad with holes is provided on the inside surface of the lid.

As mentioned above, the foam pad 29 is provided on the inside 28 of the lid 14 may be provided as having holes. FIG. 9 illustrates the situation where foam pad 29a covers at least half of the lid surface and includes a plurality of through holes 52 arrayed in a grid pattern. Specifically, the pad 29a may be approximately 3/16" thick and have 1/4" through holes 52 arrayed in a 0.5"×0.5" grid pattern (wherein the center of each hole is 0.500 inches apart) over the entire pad area. The pad's surface, which is softer than a magnet's, prevents damage to the fragile cutting edges of scalpel blades and provides sufficient grip to keep blades from sliding about. Blades laid on the perforated pad surface will inevitably bridge one or more holes. The location of this bridging provides a place to position a forceps tip under the blade to retrieve it for reinstallation on a scalpel handle when required. Should a hole not be handy, the compliance of the foam pad allows compression by the forceps tip in order to slip it beneath a blade. When a foam pad such as this is utilized, retention of the blades for disposal is accomplished by either sinking the scalpel blade tip in the adhesive filled trough or delivering it to a portion of the lid not covered by the foam and having a light coating of a sticky adhesive material 26 instead. This foam could provide double duty, functioning as a needle parking station, as well as a parking station for scalpel blades.

While embodiments of the present invention are shown and described, it is envisioned that those skilled in the art may devise various modifications of the present invention without departing from the spirit and scope of the present disclosure.

What is claimed is:

1. A needle retaining device comprising a surface; a plurality of troughs provided in said surface; and a cohesive material disposed in each of the troughs such that only a top surface of the cohesive material is exposed for receiving a point of a needle, wherein said cohesive material is configured to bond to a needle as a result of a point of the needle penetrating said top surface of said cohesive material and being captured in said cohesive material and thereafter resisting withdrawal of the needle, wherein each of said troughs includes sidewalls which are configured such that they generally prevent a captured needle from falling over.

2. A needle retaining device as recited in claim 1, wherein said cohesive material is configured such that the needle is easier to stick in the cohesive material than it is to pull the needle out of the cohesive material.

3. A needle retaining device as recited in claim 1, wherein each of said troughs is V-shaped.

4. A needle retaining device as recited in claim 1, wherein said cohesive material comprises a hot melt cohesive material.

5. A needle retaining device as recited in claim 1, further comprising a base and a lid at least one of connected and integral with said base, said lid being pivotable relative to said base, wherein said needle retaining device is openable and closeable.

6. A needle retaining device as recited in claim 5, wherein the needle retaining device is configured such that once the device is closed, the device tends to remain closed unless intentionally opened.

7. A needle retaining device as recited in claim 6, further comprising a latch structure which is configured to secure said lid and said base relative to each other.

8. A needle retaining device as recited in claim 5, further comprising a layer of cohesive material disposed on an inside surface of said lid.

9. A needle retaining device as recited in claim 5, further comprising a piece of resilient foam disposed on an inside surface of said lid.

10. A needle retaining device as recited in claim 5, further comprising a layer of cohesive material disposed on an inside surface of said lid, and a piece of resilient foam disposed on the inside surface of said lid, proximate said layer of cohesive material.

11. A needle retaining device as recited in claim 5, further comprising a magnetic surface disposed on an inside surface of said lid.

12. A needle retaining device as recited in claim 1, further comprising structure lining each of said troughs which is configured to prevent an accidentally laid needle from unintentionally contacting the cohesive material.

13. A needle retaining device as recited in claim 12, wherein said structure which is configured to prevent an accidentally laid needle from unintentionally contacting the cohesive material comprises pickets.

14. A needle retaining device as recited in claim 1, further comprising numerical indicia disposed on said surface, proximate each of said troughs, said numerical indicia configured to provide a visual counting assist of needles retained by said cohesive material.

15. A needle retaining device as recited in claim 1, wherein said cohesive material comprises an adhesive.

16. A needle retaining device as recited in claim 1, wherein said cohesive material is translucent.

17. A needle retaining device as recited in claim 1, wherein said cohesive material is homogeneous.

18. A needle retaining device as recited in claim 1, wherein said cohesive material is at least 0.060 inches deep.

19. A needle insertion technique for inserting a needle into a needle retaining device, said technique comprising: providing the needle retaining device which comprises a surface, a plurality of troughs provided in said surface such that only a top surface of the cohesive material is exposed for receiving a point of a needle, and a cohesive material disposed in each of the troughs, wherein said cohesive material is configured to bond to a needle as a result of a point of the needle penetrating said top surface of said cohesive material and being captured in said cohesive material and thereafter resisting withdrawal of the needle, said needle insertion technique further comprising sinking a point of a needle into the cohesive material such that the cohesive material becomes bonded to the needle and resists removal of the needle from the cohesive material.

20. A needle retaining device comprising a surface with an array of solid cohesive material strips of at least 0.060 inches thickness each for receiving the point of a needle wherein said cohesive material strips are retained upon said surface to bond a needle thereto as a result of the point of the needle penetrating the exposed exterior of said cohesive material and being captured in said cohesive material and thereafter resisting withdrawal of the needle; said surface having upward projecting rib features disposed adjacent said cohesive material strips to prevent an accidentally laid needle from unintentionally contacting said cohesive material strips material.

21. A needle retaining device as recited in claim 20, wherein said surface is shaped such that a plurality of troughs are provided and the cohesive material is disposed in the troughs.

22. A needle retaining device as recited in claim 21, wherein each of said troughs is V-shaped.

23. A needle retaining device as recited in claim 21, wherein each of said troughs includes sidewalls which are configured such that they generally prevent the needle from falling over.

24. A needle retaining device as recited in claim 21, further comprising numerical indicia disposed on said surface, proximate each of said troughs, said numerical indicia configured to provide a visual counting assist of needles retain by said cohesive material.

25. A needle retaining device as recited in claim 20, wherein said cohesive material is configured such that the needle is easier to stick in the cohesive material than it s to pull the needle out of the cohesive material.

26. A needle retaining device as recited in claim 20, wherein said cohesive material comprises a hot melt cohesive material.

27. A needle retaining device as recited in claim 20, further comprising a base and a lid being at least one of connected and integral with said base, said lid being pivotable relative to said base, wherein said needle retaining device is openable and closeable.

28. A needle retaining device as recited in claim 27, wherein the needle retaining device is configured such that once the device is closed, the device tends to remain closed unless intentionally opened.

29. A needle retaining device as recited in claim 28, further comprising a latch structure which is configured to secure said lid and said base relative to each other.

30. A needle retaining device as recited in claim 27, further comprising a layer of cohesive material disposed on an inside surface of said lid.

31. A needle retaining device as recited in claim 27, further comprising a piece of resilient foam disposed on an inside surface of said lid.

32. A needle retaining device as recited in claim 27, further comprising a layer of cohesive material disposed on an inside surface of said lid, and a piece of resilient foam disposed on the inside surface of said lid, proximate said layer of cohesive material.

33. A needle retaining device as recited in claim 27, further comprising a magnetic surface disposed on an inside surface of said lid.

34. A needle retaining device as recited in claim 20, wherein said cohesive material comprises an adhesive.

35. A needle retaining device as recited in claim 20, wherein said cohesive material is translucent.

36. A needle retaining device as recited in claim 20, wherein said cohesive material is homogeneous.

* * * * *

UNITED STATES PATENT AND TRADEMARK OFFICE
CERTIFICATE OF CORRECTION

PATENT NO. : 7,070,051 B2  Page 1 of 1
APPLICATION NO. : 11/010067
DATED : July 4, 2006
INVENTOR(S) : Rowland W. Kanner and Larry Lee Young It is certified that error appears in the above-identified patent and that said Letters Patent is hereby corrected as shown below:

Column 13, Lines 15-16 "strips material." should be
-- strips. --
Column 13, Line 31 " retain " should be -- retained --
Column 13, Line 34 "s " should be -- is --

Signed and Sealed this

Twenty-first Day of November, 2006

JON W. DUDAS
*Director of the United States Patent and Trademark Office*